United States Patent [19]

Gavrilovic et al.

[11] 4,029,594
[45] June 14, 1977

[54] NOVEL LIQUID CRYSTAL COMPOUNDS AND ELECTRO-OPTIC DEVICES INCORPORATING THEM

[75] Inventors: Dragan Milan Gavrilovic, Cranbury; Daniel Louis Ross, Princeton, both of N.J.

[73] Assignee: RCA Corporation, New York, N.Y.

[22] Filed: June 17, 1976

[21] Appl. No.: 696,905

[52] U.S. Cl. .................... 252/299; 252/408; 260/463; 260/465 D; 260/465 F; 260/465 G; 350/160 LC

[51] Int. Cl.² .................. C09K 3/34; G02F 1/13; C07C 121/64; C07C 69/96

[58] Field of Search .............. 252/299, 408; 350/160 LC; 260/463, 465 D, 465 F, 465 G

[56] References Cited

UNITED STATES PATENTS

| 3,836,478 | 9/1974 | Green et al. | 252/299 |
|---|---|---|---|
| 3,915,883 | 10/1975 | Van Meter et al. | 252/299 |
| 3,947,375 | 3/1976 | Gray et al. | 252/299 |
| 3,951,846 | 4/1976 | Gavrilovic | 252/299 |
| 3,953,491 | 4/1976 | Steinstrasser et al. | 252/299 |

FOREIGN PATENTS OR APPLICATIONS

| 2,502,904 | 7/1975 | Germany | 252/299 |
|---|---|---|---|
| 4,995,880 | 9/1974 | Japan | 252/299 |

OTHER PUBLICATIONS

Gray, G. W., et al., Liquid Crystals & Plastic Crystals, vol. 1, Ellis Horwood, Ltd., London, pp. 103–152 (1974).
Arora, S. L., et al., J. Org. Chem., vol. 35, No. 12 pp. 4055–4058 (1970).

Primary Examiner—Richard E. Schafer
Assistant Examiner—T. S. Gron
Attorney, Agent, or Firm—Glenn H. Bruestle; Birgit E. Morris

[57] ABSTRACT

Liquid crystal compounds of the formula

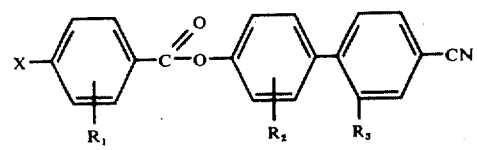

wherein X can be alkyl (R-), alkoxy (RO-), acyloxy

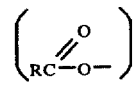

or alkylcarbonato

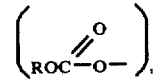

wherein R is an alkyl group from 1–10 carbon atoms, and $R_1$–$R_3$ can be hydrogen, methyl or halogen with the proviso that at least one and no more than two of $R_1$–$R_3$ are substituents other than hydrogen, have positive dielectric anisotropy and are useful in electro-optic devices which comprise a thin liquid crystal layer between two closely spaced parallel electrodes.

9 Claims, 1 Drawing Figure

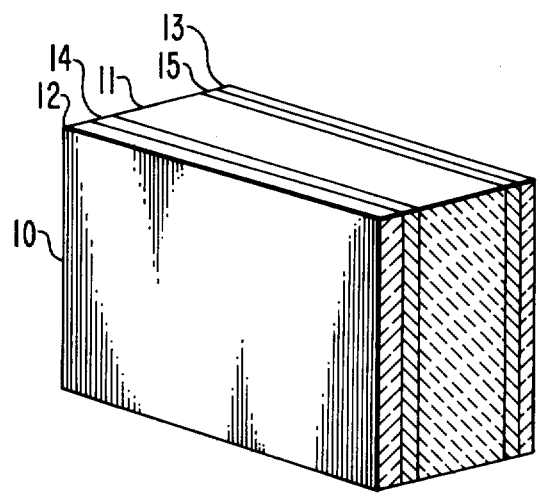

NOVEL LIQUID CRYSTAL COMPOUNDS AND ELECTRO-OPTIC DEVICES INCORPORATING THEM

This invention relates to novel liquid crystal compounds and to electro-optic devices including them. More particularly, this invention relates to nematic liquid crystal compounds having positive dielectric anisotropy and to field effect liquid crystal cells.

BACKGROUND OF THE INVENTION

Mesomorphic or liquid crystal compositions are of increasing interest in a variety of electro-optic display devices. Liquid crystal compositions are of particular interest for electrically controllable, flat panel displays such as watch faces, digital clocks, calculator displays, numeric displays for instruments and the like. An electro-optic device, e.g., a liquid crystal cell, comprises a layer of a liquid crystal composition between two closely spaced parallel conductive plates, at least one of which is transparent. When the conductive plates are connected to a source of voltage, an electric field is generated in the liquid crystal composition.

Field effect liquid crystal devices contain nematic compounds or mixtures of liquid crystal compounds having positive dielectric anisotropy. The conductive plates have been treated so that the liquid crystal molecules align themselves in a particular direction, usually parallel, to the plane of the plates. When an electric field is applied, the positive dielectric anisotropy of the molecules causes them to realign themselves in a direction parallel to the applied field and perpendicular to the plates. The change in alignment is made visible using a polarizer and an analyzer on either side of the cell. Field effect liquid crystal cells have the advantages of lower threshold voltages and wider viewing angle than other electro-optic devices such as dynamic scattering cells, and they have excellent contrast and long lifetimes.

U.S. Pat. No. to Gavrilovic, 3,951,846, incorporated herein by reference, discloses liquid crystal compounds having high and broad use temperature ranges which have the formula

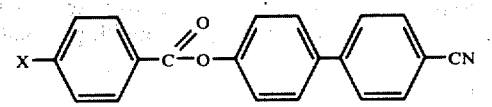

wherein X can be hydrogen, alkyl, alkoxy, acyloxy or alkylcarbonato wherein the alkyl groups have 1-10 carbon atoms. These liquid crystal compounds have positive dielectric anisotropy and are useful in field effect liquid crystal devices.

Each mesomorphic compound has a particular temperature range in which it is an ordered liquid, ranging from the solid to nematic liquid crystal melting point, up to the temperature at which it forms an isotropic liquid. This is the temperature range useful in electro-optic cells. Although, as is known, wide variations in use temperature ranges can be effected by employing mixtures of liquid crystal compounds that are compatible with each other rather than single compounds, no single liquid crystal compound or mixture of compounds now known can satisfy all of the use temperature ranges that are desired. The particular mesomorphic temperature range for each compound or even whether a compound will be mesomorphic or not is on the whole unpredictable. Thus, new liquid crystal compounds which have different use temperature ranges are being sought to satisfy various temperature requirements for which the liquid crystal cells will be employed.

SUMMARY OF THE INVENTION

It has been discovered that certain liquid crystal compounds derived from substituted 4-cyano-4'-hydroxybiphenyls and substituted or unsubstituted benzoyl chlorides have positive dielectric anisotropy and are useful in field effect liquid crystal cells. Certain of the compounds have very broad mesomorphic temperature ranges.

BRIEF DESCRIPTION OF THE DRAWING

The FIGURE is a cross-sectional perspective view of an electro-optic device embodying the invention.

DETAILED DESCRIPTION OF THE INVENTION

The novel liquid crystal compounds have the formula

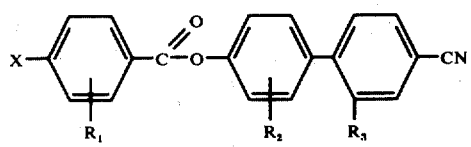

wherein X is alkyl (R—), alkoxy (RO—), acyloxy

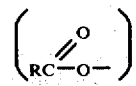

or alkylcarbonato

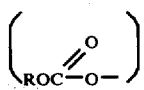

wherein R is an alkyl group of 1–10 carbon atoms and $R_1$–$R_3$ can be hydrogen, methyl or halogen with the proviso that at least one and no more than two of $R_1$–$R_3$ are substituents other than hydrogen. The alkyl groups include straight chain and branched chain alkyl groups, but at the present time straight chain alkyl groups are preferred. These compounds can be employed in electro-optic devices alone, in admixture with each other, or in admixture with other liquid crystal compounds to broaden the use temperature range or vary the response of the device.

The present compounds can be prepared by reacting a 4-cyano-4'-hydroxybiphenyl, wherein the biphenyl group can be substituted with a methyl or a halogen group with a substituted or unsubstituted benzoyl chloride. The resultant nematic liquid crystal compounds can be purified by conventional manner, as by recrystallization, fractional distillation or chromatography.

Referring to the FIGURE, a liquid crystal cell 10 comprises a layer of a liquid crystal composition 11 between a front transparent support plate 12 and a back support plate 13. The front glass support plate 12 is coated on the inside surface thereof with a transparent conductive layer 14 as of tin oxide, to form an electrode. The back support plate 13 is also provided on the inside surface thereof with a conductive layer 15 to form the other electrode. If light is to be transmitted through the cell, the back electrode 15 and the back support plate 13 are also transparent and made of the same materials as the front support plate 12 and front electrode 14. If the liquid crystal cell is to reflect light, the back electrode 15 can be made reflective, e.g., coated with aluminum. As is known, additional compounds such as wetting agents, aligning agents and the like can be added to the liquid crystal composition to improve the optical or electrical performance of the cell. In operation, the electrode 14 and 15 are connected to a source of volage (not shown). The electro-optic devices described above can be incorporated into various displays, such as electronic clocks, watches, advertising displays, numeric indicators and the like.

The invention will be further illustrated by the following examples but it is to be understood that the invention is not limited to the details described therein. In the examples, parts and percentages are by weight unless otherwise noted.

The mesomorphic transition temperatures of the compounds prepared in the examples were determined using a Thomas Hoover melting point apparatus, a differential scanning calorimeter and a polarizing hot stage microscope in conventional manner.

EXAMPLE 1

Preparation of 4-cyano-4'-biphenyl(4-heptyloxy-2-methyl)benzoate

Part A

Twenty-five parts of 4-hydroxy-2-methylacetophenone, 46 parts of potassium carbonate and 34.3 parts of 1-bromoheptane were stirred in 148 parts by volume of cyclohexanone and refluxed for 2 hours. The product was filtered and the solvent evaporated leaving an oily residue. This material was distilled at 150°–152° C. at 0.09 mm Hg to obtain 34.0 parts (82.5% yield) of 4-heptyloxy-2-methylacetophenone.

Part B

To a cold solution of 80 parts of sodium hydroxide in 400 parts of water were added 88.4 parts of bromine. This solution was stirred into a solution of 31 parts of the product of Part A in 280 parts by volume of dioxane. After stirring for three hours at 50° C., 18.5 parts of sodium bisulfite were stirred in for one-half hour. The concentrated hydrochloric acid was added in small increments to acidify the mixture. The aqueous layer was separated, washed twice with 250 parts by volume of benzene and the washings combined with the organic layer. The organic material was dried over magnesium sulfate, the solvent evaporated and the solid product collected. The product was recrystallized from hexane to obtain 29.0 parts (93% yield) of 4-heptyloxy-2-methylbenzoic acid having a melting point of 74°–76° C.

Part C

The product obtained in Part B was refluxed overnight with 50 parts by volume of thionyl chloride and b 50 parts by volume of benzene under anhydrous conditions. The solvent and excess thionyl chloride were evaporated and the product distilled at 150° C. at 0.2 mm Hg to obtain 29.7 parts (95.5% yield) of 4-heptyloxy-2-methylbenzoyl chloride as a colorless liquid.

Part D 2.7 parts of the product of Part C, 1.95 parts of 4-cyano-4'-hydroxybiphenyl, 3 parts by volume of pyridine and 20 parts by volume of benzene were refluxed for one hour and filtered. The filtrate was washed twice with 50 parts by volume of dilute (3.6%) hydrochloric acid and then with saturated aqueous sodium chloride. The organic layer was separated, dried over magnesium sulfate and the solvent evaporated. The resultant solid product was recrystallized twice from acetone.

One part of the product, 4-cyano-4'-biphenyl(4-heptyloxy-2-methyl)benzoate having the structure

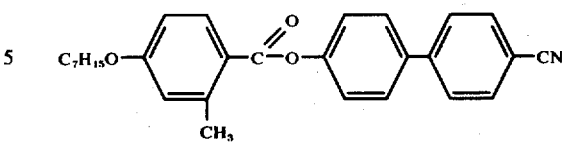

(23% yield) was obtained having a solid to nematic transition temperature (CN) of 78.5°–80° C. and a nematic to isotropic liquid transition temperature (NL) of 176.5° C. The heat of fusion was 9.7 kcal/mol.

EXAMPLE 2

Preparation of 4-cyano-4'-biphenyl(4-butylcarbonato-2-methyl)benzoate.

Part A

The procedure of Example 1, Part A was followed except substituting benzylbromide as the bromo compound. The oily residue was distilled at 160° C. at 0.07 mm Hg to obtain 100% yield of 4-benzyloxy-2-methylacetophenone.

Part B

The procedure of Example 1, Part B was followed except substituting the above acetophenone product. The crude product was recrystallized from cyclohexane to obtain a 78% yield 4-benzyloxy-2-methylbenzoic acid having a melting point of 126°–129° C.

Part C

A solution of 6.5 parts of the product of Part B in 200 parts by volume of ethanol was hydrogenated in a Parr apparatus using 0.3 part of 10% palladium on carbon catalyst with an initial pressure of 50 psi. After 2.5 hours the reaction mixture was filtered, the solvent evaporated and the residue recrystallized from water. 3.3 Parts of 4-hydroxy-2-methylbenzoic acid (80.5% yield) was obtained having a melting point of 174.5°–176.5° C.

Part D

To a cold solution of 1.52 parts of the product of Part C, 0.8 part of sodium hydroxide and 20 parts of water was slowly added 1.37 parts of n-butylchloroformate. The reaction mixture was stirred at 0°–10° C. for 0.5 hour and extracted with 30 parts by volume of ether. The aqueous solution was acidified with concentrated hydrochloric acid and extracted with ether. The ether extracts were combined, dried over sodium sulfate and the solvent evaporated. The product was 4-butylcarbonato-2-methylbenzoic acid.

Part E

The procedure of Example 1, Part C was followed except substituting the product of Part D as the substituted methylbenzoic acid. The crude product was vacuum distilled at 123°–124° C. at 0.07 mm Hg to obtain 4-n-butylcarbonato-2-methylbenzoyl chloride.

Part F

The procedure of Example 1, Part D was followed except substituting the product of Part E as the substituted benzoyl chloride. The product was recrystallized from cyclohexane.

4-Cyano-4'-biphenyl(4-n-butylcarbonato-2-methyl)-benzoate had a CN of 97°–98° C. and NL of 200° C. The formula is

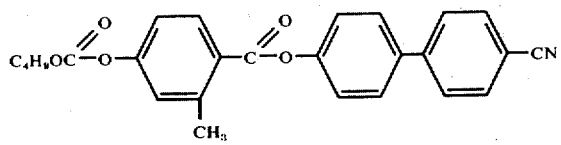

The heat of fusion was 8.1 kcal/mol.

EXAMPLE 3

Preparation of 4-cyano-4'-biphenyl(4-hexanoyloxy-2-methyl)benzoate

Part A

A mixture of 3.04 parts of 4-hydroxy-2-methylbenzoic acid, 8.57 parts of hexanoic anhydride, one drop of concentrated sulfuric acid and 3 parts by volume of benzene were refluxed for 15 minutes when the mixture was poured over ice and stirred for 10 minutes. The mixture was extracted three times with 100 parts by volume of chloroform. The combined extracts were dried over magnesium sulfate and the solvent evaporated to obtain 4-hexanoyloxy-2-methylbenzoic acid.

Part B

Using the product obtained in Part A, the procedure of Example 1, Part C was followed to obtain the corresponding acid chloride. The product was purified by distillation at 135° C. at 0.07 mm Hg.

Part C

The procedure of Example 1, Part D was followed except substituting 4-hexanoyloxy-2-methylbenzoyl chloride as the benzoyl chloride compound. The crude product was recrystallized from cyclohexane and then isopropanol.

4-Cyano-4'-biphenyl(4-hexanoyloxy-2-methyl)benzoate having the formula

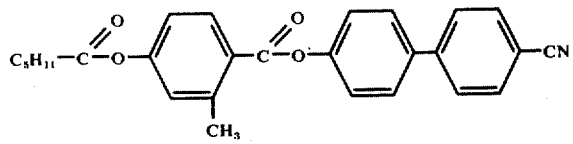

was obtained in 47.5% yield. The CN temperature was 92.5°–93.5° C. and NL temperature was 196° C. The heat of fusion was 9.4 kcal/mol.

EXAMPLE 4

Preparation of 4-cyano-4'-biphenyl(4-heptyloxy-2-chloro)benzoate

Part A

A mixture of 4.0 parts of 2-chloro-4-hydroxybenzoic acid, 8.3 parts of 1-bromoheptane, 2.6 parts of potassium hydroxide, 10 parts of water and 90 parts by volume of ethanol was refluxed for 20 hours. A solution of 2.5 parts of potassium hydroxide in 50 hours. A solution of 2.5 parts of potassium hydroxide in 50 parts of water was then added and refluxing continued for an additional 1.5 hours. The reaction mixture was dilated with 100 parts of water, acidified with concentrated hydrochloric acid and extracted with methylene chloride. The combined extracts were dried over sodium sulfate, the solvent evaporated and the resultant residue recrystallized from hexane. 4.5 Parts of 4-heptyloxy-2-chlorobenzoic acid (75% yield) was obtained having a melting point of 76°–78° C.

Part B

The procedure of Example 1, Part C was followed except substituting the above product as the benzoic acid compound. 4-heptyloxy-2-chlorobenzoyl chloride was purified by distillation at 140°–142° C. at 0.07 mm Hg.

Part C

The procedure of Example 1, Part D was followed except substituting the above benzoyl chloride compound.

4-Cyano-4'-biphenyl (4-heptyloxy-2-chloro)benzoate was purified by recrystallizing from cyclohexane and then from isopropanol. A 61% yield was obtained. This compound has the formula

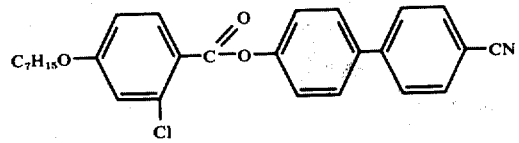

a CN temperature of 100°–101° C. and an NL temperature of 171.5° C. The heat of fusion was 7.0 kcal/mol.

EXAMPLE 5

Preparation of 4-cyano-4'-biphenyl(4-butylcarbonato-2-chloro)benzoate

The procedure of Example 2, Parts D, E and F was followed employing as the starting benzoic acid, 2-chloro-4-hydroxybenzoic acid.

The product was recrystallized first from cyclohexane and second from 9:1 isopropanol/ethylacetate to yield the compound

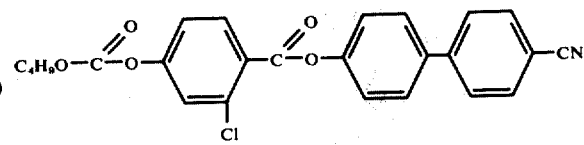

which has a CN temperature of 82°–83° C. and an NL temperature of 200° C. The heat of fusion was 7.1 kcal/mol.

EXAMPLE 6

Preparation of 4-cyano-4'-biphenyl(4-hexanoyloxy-2-chloro)benzoate

The procedure of Example 3 was followed except substituting 4-hydroxy-2-chlorobenzoic acid for the corresponding methyl-substituted benzoic acid.

The product was recrystallized from isopropanol to obtain

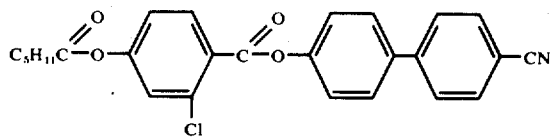

which had a CN temperature of 60° C. and an NL temperature of 200° C. The heat of fusion was 5.4 kcal/mol.

EXAMPLE 7

Preparation of 4-cyano-2-methyl-4'-biphenyl(4-heptyloxy)benzoate

Part A

4-Bromo-2-methyl aniline was reacted in accordance with the Gomberg-Bachman reaction via the diazonium salt and benzene in the presence of sodium acetate. The reaction was heated to about 30° C. The product, 4-bromo-2-methylbiphenyl was purified by distilling at 106°–108° C. at 0.2 mm Hg. A 40% yield was obtained.

Part B

To a suspension of 8.4 parts of aluminum chloride in 16 parts by volume of carbon disulfide was added dropwise a solution of 12.3 parts of 4-bromo-2-methylbiphenyl, 4.2 parts of acetyl chloride and 16 parts by volume of carbon disulfide. The reaction mixture was stirred for 0.5 hour, refluxed for 2 hours, then poured over 100 parts of ice and water and extracted with methylene chloride. The combined extracts were washed with water, dried over sodium sulfate and the solvent evaporated.

After recrystallizing from hexane, 6.6 parts (46% yield) of 4-bromo-2-methyl-4'-acetylbiphenyl was obtained having a melting point of 84°–86° C.

Part C 2.9 Parts of the above product was suspended in 5.6 parts of disodium phosphate and 30 parts by volume of methylene chloride. An ice cold solution of 5 parts of methylene chloride, 0.42 part of 90% hydrogen peroxide and 3.8 parts of trifluoroacetic acid, all parts by volume, was added dropwise to the suspension while stirring vigorously. The reaction mixture was refluxed for 1.5 hours, poured into 100 parts of water and the organic layer collected, dried over magnesium sulfate and the solvent evaporated to leave an oil, 4-bromo-2-methyl-4'-biphenyl acetate.

Part D

A solution of 6.1 parts of the above product, 5.0 parts of potassium hydroxide, 5 parts of water and 40 parts by volume of methanol was refluxed for 2 hours. The reaction mixture was diluted with 50 parts of water, acidified with hydrochloric acid and extracted with five 50 part portions of methylene chloride. The combined extracts were dried over magnesium sulfate and the solvent evaporated. 4.4 Parts (87% yield) of 4-bromo-2-methyl-4'-hydroxybiphenyl was obtained as a solid from hexane.

Part E 4.2 Parts of the above product, 2.0 parts of cuprous cyanide and 20 parts by volume of dimethylformamide were mixed and refluxed for 17 hours. The mixture was poured into 100 parts of 18% hydrochloric acid, 100 parts by volume of methylene chloride was stirred in and the phases separated. The organic phase was dried over sodium sulfate and the solvent evaporated. The product was chromatographed through a silica gel column with benzene as eluent and recrystallized from 200 parts by volume of an 8.2 mixture of methylcyclohexane and toluene. 2.2 Parts (67% yield) of 4-cyano-2-methyl-4'-hydroxybiphenyl was obtained having a melting point of 136.5°–137.5° C.

Part F

The procedure of Example 1, Part D was followed substituting the above compound as the hydroxydiphenyl and p-heptyloxybenzoyl chloride as the benzoyl chloride compound. The product was recrystallized first from cyclohexane and then from isopropanol.

A 50% yield of 4-cyano-2-methyl-4'-biphenyl(4-heptyloxy)-benzoate having the formula

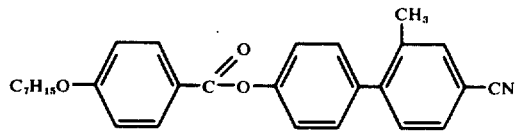

was obtained. This compound had a CN temperature of 104°–105° C. and an NL temperature of 160° C. The heat of fusion was 10.6 kcal/mol.

EXAMPLE 8

Preparation of 4-cyano-2-methyl-4'-biphenyl(4-n-butylcarbonato)-benzoate

The procedure of Example 2 was followed except substituting 4-cyano-2-methyl-4'-hydroxybiphenyl as the hydroxybiphenyl compound and 4-n-butylcarbonatobenzoyl chloride as the benzoyl chloride compound.

The product was recrystallized from cyclohexane to obtain 4-cyano-2-methyl-4'-biphenyl(4-n-butylcarbonato)-benzoate having the formula

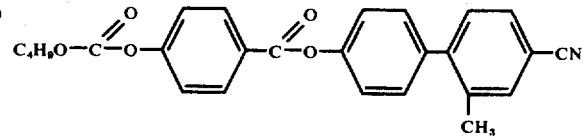

This compound had a CN temperature of 119°–120° C. and an NL temperature of 184° C. The heat of fusion was 8.2 kcal/mol.

EXAMPLE 9

Preparation of 4-cyano-2-methyl-4'-biphenyl(4-hexanoyloxy)benzoate

The procedure of Example 3 was followed except substituting 4-cyano-2-methyl-4'-hydroxybiphenyl as the hydroxybiphenyl compound and p-hexanoyloxybenzoyl chloride as the benzoyl chloride compound.

The product was recrystallized from cyclohexane to obtain 4-cyano-2-methyl-4'-biphenyl(4-hexanoyloxy)-benzoate having the formula

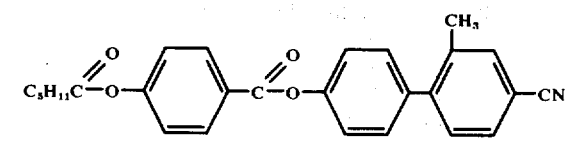

This compound had a CN temperature of 108°–109° C. and an NL temperature of 176° C. The heat of fusion was 8.5 kcal/mol.

EXAMPLE 10

Preparation of 4-cyano-2-methyl-4'-biphenyl (4-butylcarbonato-2-chloro)benzoate

The procedure of Example 5, Part C was followed except substituting 4-cyano-2-methyl-4'-hydroxybiphenyl as the hydroxybiphenyl compound.

The product, 4-cyano-2-methyl-4'-biphenyl(4-butylcarbanato-2-chloro)benzoate was recrystallized from cyclohexane. This compound has the formula

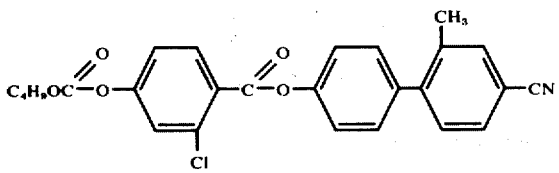

a CN temperature of 98°–99° C. and an NL temperature of 116.5° C. The heat of fusion was 6.1 kcal/mol.

EXAMPLE 11

Preparation of 4-cyano-2-methyl-4'-biphenyl(2-chloro-4-hexanoyloxy)benzoate

The procedure of Example 6, Part C was followed except substituting 4-cyano-2-methyl-4'-hydroxybiphenyl as the hydroxybiphenyl compound.

The product, after recrystallizing from cyclohexane and then isopropanol, has the formula

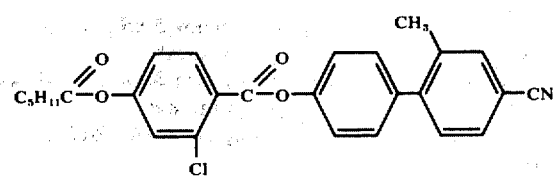

a CN temperature of 99°–100° C. and an NL temperature of 111° C. The heat of fusion was 6.0 kcal/mol.

EXAMPLE 12

Preparation of 4-cyano-4'-biphenyl(4-heptyloxy-3-chloro)benzoate

The procedure of Example 4, Part C was followed except substituting 3-chloro-4-heptyloxybenzoyl chloride as the benzoyl chloride compound.

The product, after recrystallizing from isopropanol and then from cyclohexane, has the formula

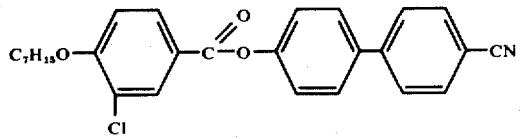

a crystal to smectic transition temperature (CS) of 89° C., a smectic to nematic transition temperature (SN) of 133.5° C. and an NL temperature of 191.0° C. The heat of fusion was 15.7 kcal/mol.

EXAMPLE 13

Preparation of 4-cyano-4'-biphenyl(3-chloro-4-hexanoyloxy)benzoate

The procedure of Example 6, Part C was followed except substituting 3-chloro-4-hexanoyloxybenzoyl chloride as the benzoyl chloride compound.

The product, after recrystallizing from cyclohexane and then with isopropanol, has the formula

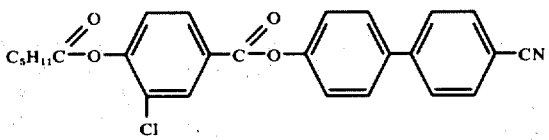

a CN temperature of 87.0° C. and an NL temperature of 224° C. The heat of fusion was 5.1 kcal/mol.

EXAMPLE 14

Preparation of 4-cyano-4'-biphenyl(4-butylcarbonato-3-chloro)benzoate

The procedure of Example 5, Part C was followed except that 4-butylcarbonato-3-chlorobenzoyl chloride was substituted as the benzoyl chloride compound.

The product, after recrystallizing from isopropanol and then twice from cyclohexane, has the formula

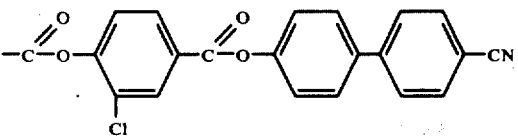

a CS temperature of 100.0° C., an SN temperature of 104.0° C. and an NL temperature of 197.5° C. The heat of fusion was 17.2 kcal/mol.

Generally commenting on the relationship of structure to properties for the above compounds, it can be seen that although the mesomorphic temperature range is not directly related to structure, those compounds which are doubly substituted, i.e., those of Examples 10 and 11, tend to have the a narrowest use temperature ranges. The compound having the formula

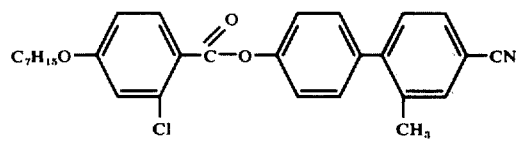

is in fact monotropic, having a melting point of 99°–101° C. with an isotropic to nematic transition temperature at 86° C.

Compounds having a meta substituent, see Examples 12 and 14, tend to have high heats of fusion, although in this regard the compound of Example 13 is an anomaly. The lower the heat of fusion of individual components of the liquid crystal mixture, the lower the eutectic temperature of the mixture. Thus, liquid crystal compositions having a low and broad use temperature range can be provided by mixing compounds having low heats of fusion and high nematic to liquid transition temperatures.

In addition to the nematic and smectic mesophases, the present compounds can exhibit the cholesteric mesophase when the compound has a branched chain alkyl group having an assymmetric carbon atom.

EXAMPLE 15

A mixture was made using 1.6 parts of the compound of Example 6, 1.0 parts of the compound of Example 13 and 2.83 parts of p-n-pentyl-p'cyanodiphenyl. This mixture had a CN temperature of 12° C. and an NL temperature of 93.6° C.

The mixture was charged to a liquid crystal cell as in the Figure. The threshold voltage was 1.2 volts at an ambient temperature of about 22° C. and at 6 volts, the on response time was about 100 milliseconds and the off response time was about 500 milliseconds.

We claim:

1. In an electro-optic cell comprising a liquid crystal layer between two electrodes, the improvement which comprises emloying as the liquid crystal a compound of the formula

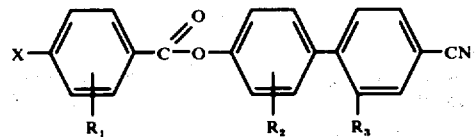

wherein X can be an alkyl, (R) alkoxy (OR), acyloxy (

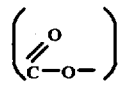

or alkylcarbonate (

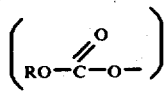

group wherein R is a alkyl group containing carbon atoms and $R_1$–$R_3$ can be hydrogen, methyl or halogen with the proviso that at least one and no more than two of $R_1$–$R_3$ are substituents other than hydrogen.

2. An electro-optical cell according to claim 1 wherein both electrodes are transparent.

3. A liquid crystal compound having the formula

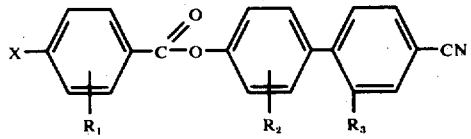

wherein X can be alkyl (R–), alkoxy (-OR), acyloxy

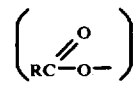

or alkylcarbonato

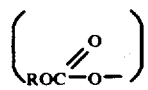

group wherein R is an alkyl group containing 1–10 carbon atoms and $R_1$–$R_3$ can be hydrogen, methyl or halogen with the proviso that at least one and no more than two of $R_1$–$R_3$ substituents other than hydrogen.

4. A compound according to claim 3 wherein $R_1$ is chlorine.

5. A compound according to claim 3 wherein $R_1$ is methyl.

6. A compound according to claim 3 wherein $R_2$ is hydrogen and $R_3$ is methyl.

7. A compound according to claim 3 wherein $R_1$ is chlorine, $R_2$ is hydrogen and $R_3$ is methyl.

8. A compound according to claim 3 wherein $R_1$ is methyl, $R_2$ is hydrogen and $R_3$ is methyl.

9. 4-Cyano-4'-biphenyl(4-hexanoyloxy-2-chloro)-benzoate.

* * * * *